United States Patent
Santos et al.

(10) Patent No.: US 12,016,713 B2
(45) Date of Patent: Jun. 25, 2024

(54) MINI C-ARM WITH INCREASED RANGE OF MOTION

(71) Applicant: HOLOGIC, INC., Marlborough, MA (US)

(72) Inventors: Daniel Santos, Westborough, MA (US); Christian Ulm, Hopkinton, MA (US); Tri Pham, Charlestown, MA (US); Christopher O. Evans, Amherst, NH (US); Anthony Clegg Parker, New Ipswich, NH (US)

(73) Assignee: Hologic, Inc., Marlborough, MA (US)

( * ) Notice: Subject to any disclaimer, the term of this patent is extended or adjusted under 35 U.S.C. 154(b) by 557 days.

(21) Appl. No.: 17/280,020

(22) PCT Filed: Sep. 26, 2019

(86) PCT No.: PCT/US2019/053144
§ 371 (c)(1),
(2) Date: Mar. 25, 2021

(87) PCT Pub. No.: WO2020/069122
PCT Pub. Date: Apr. 2, 2020

(65) Prior Publication Data
US 2022/0031267 A1     Feb. 3, 2022

Related U.S. Application Data

(60) Provisional application No. 62/738,149, filed on Sep. 28, 2018.

(51) Int. Cl.
*A61B 6/00* (2006.01)
(52) U.S. Cl.
CPC .......... *A61B 6/4405* (2013.01); *A61B 6/4441* (2013.01)

(58) Field of Classification Search
None
See application file for complete search history.

(56) References Cited

U.S. PATENT DOCUMENTS

| 5,642,395 A | 6/1997 | Anderton et al. |
| 6,669,365 B2 | 12/2003 | Iinuma |
| (Continued) |

FOREIGN PATENT DOCUMENTS

| CN | 102793549 A | 11/2012 |
| CN | 103371842 A | 10/2013 |
| (Continued) |

OTHER PUBLICATIONS

International Search Report and Written Opinion for International application No. PCT/US2019/053144, dated Jan. 15, 2020, 8 pages.
(Continued)

*Primary Examiner* — Hoon K Song
(74) *Attorney, Agent, or Firm* — Merchant & Gould P.C.

(57) ABSTRACT

A mobile imaging system or mini C-arm with an increased range of motion is disclosed. The mini C-arm including a mobile base, a C-arm assembly, and an arm assembly for coupling the C-arm assembly and the mobile base. The arm assembly being coupled to the mobile base via a first joint assembly that enables the arm assembly to move relative to the mobile base about first and second axes of rotation. Thus, in use, the first joint assembly enables two degrees of motion—a first vertical pivoting or rotational movement and a second horizontal pivoting or rotational movement. The first joint assembly being coupled to the base via a horizontal axis of rotation that is located at a vertically fixed position so that the horizontal axis of rotation is positioned at a fixed height or distance from the base, and hence a fixed height or distance from the floor.

13 Claims, 8 Drawing Sheets

(56) References Cited

U.S. PATENT DOCUMENTS

| | | |
|---|---|---|
| 6,979,123 B2 | 12/2005 | Barta et al. |
| 7,016,457 B1 | 3/2006 | Senzig et al. |
| 7,434,996 B2 | 10/2008 | Wang et al. |
| 7,603,155 B2 | 10/2009 | Jensen |
| 7,607,183 B2 | 10/2009 | Somasundaram et al. |
| 7,607,832 B2 | 10/2009 | Jensen et al. |
| 7,720,523 B2 | 5/2010 | Omernick et al. |
| 8,182,150 B2 | 5/2012 | Gorges et al. |
| 8,208,988 B2 | 6/2012 | Jensen |
| 8,430,564 B2 | 4/2013 | Simmons et al. |
| 8,465,203 B2 | 6/2013 | Barker et al. |
| 8,641,277 B2 | 2/2014 | Simmons et al. |
| 8,666,585 B2 | 3/2014 | Bouvier |
| 8,708,561 B2 | 4/2014 | Eaves |
| 8,824,638 B2 | 9/2014 | Nicholson et al. |
| 8,849,370 B2 | 9/2014 | Bouvier |
| 8,899,834 B2 | 12/2014 | Barker et al. |
| 8,942,346 B2 | 1/2015 | Nicholson et al. |
| 9,025,730 B2 | 5/2015 | Barker et al. |
| 9,033,575 B2 | 5/2015 | Martinez Ferreira |
| 9,125,611 B2 | 9/2015 | Eaves |
| 9,265,470 B2 | 2/2016 | Simmons et al. |
| 9,295,521 B2 | 3/2016 | Pack et al. |
| 9,398,675 B2 | 7/2016 | Eaves |
| 9,402,639 B2 | 8/2016 | Lloyd et al. |
| 9,510,798 B2 | 12/2016 | Mao et al. |
| 9,532,757 B2 | 1/2017 | Claus et al. |
| 9,552,898 B2 | 1/2017 | Nicholson et al. |
| 9,693,437 B2 | 6/2017 | Simmons et al. |
| 2001/0005410 A1 | 6/2001 | Rasche |
| 2008/0013692 A1* | 1/2008 | Maschke .............. B25J 11/00 |
| | | 378/198 |
| 2009/0180592 A1 | 7/2009 | Gross et al. |
| 2010/0054423 A1 | 3/2010 | Noda |
| 2010/0239073 A1* | 9/2010 | Eaves .............. A61B 6/4405 |
| | | 378/198 |
| 2012/0029694 A1 | 2/2012 | Muller |
| 2013/0272499 A1 | 10/2013 | Simmons et al. |
| 2014/0192962 A1 | 7/2014 | Eaves |
| 2015/0055760 A1 | 2/2015 | Barker et al. |
| 2015/0071412 A1 | 3/2015 | Simmons et al. |
| 2015/0201893 A1 | 7/2015 | Bouvier et al. |
| 2015/0320370 A1 | 11/2015 | Bouvier et al. |
| 2015/0335302 A1 | 11/2015 | Eaves |
| 2016/0000391 A1 | 1/2016 | Galloni |
| 2016/0070004 A1 | 3/2016 | Liu |
| 2016/0228074 A1 | 8/2016 | Riddell et al. |
| 2018/0271461 A1 | 9/2018 | Simmons |
| 2018/0279980 A1 | 10/2018 | Barker et al. |
| 2018/0296174 A1 | 10/2018 | Barker et al. |
| 2018/0298970 A1 | 10/2018 | Daugirdas et al. |

FOREIGN PATENT DOCUMENTS

| | | |
|---|---|---|
| CN | 105605379 A | 5/2016 |
| CN | 108495588 A | 9/2018 |
| DE | 10 2012 217606 | 3/2014 |
| DE | 10 2014 206301 | 3/2015 |
| DE | 10 2015 207736 | 11/2016 |
| EP | 2408375 B1 | 6/2017 |
| JP | 2001-218757 A | 8/2001 |
| JP | 2008-018240 A | 1/2008 |
| JP | 2008-168128 A | 7/2008 |
| JP | 2010-082431 A | 4/2010 |
| WO | 00/19783 | 4/2000 |
| WO | 2010/108146 | 9/2010 |

OTHER PUBLICATIONS

PCT International Preliminary Report on Patentability in Application OCT/US2019/053144, dated Apr. 8, 2021, 7 pages.

European Extended Search Report in Application 19867073, dated May 24, 2022, 7 pages.

* cited by examiner

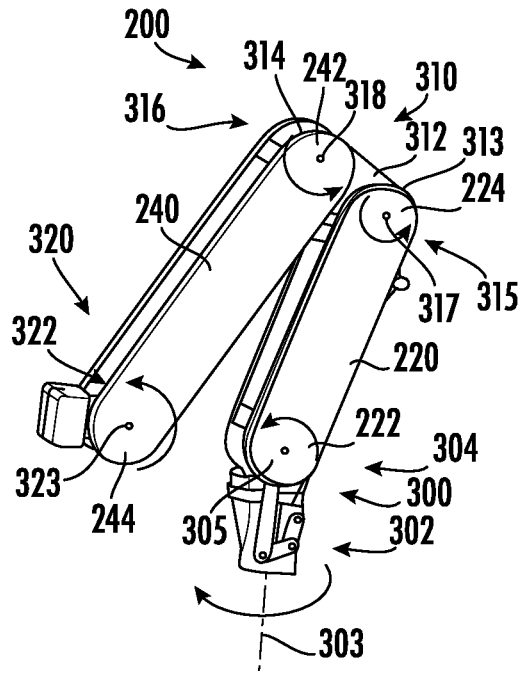
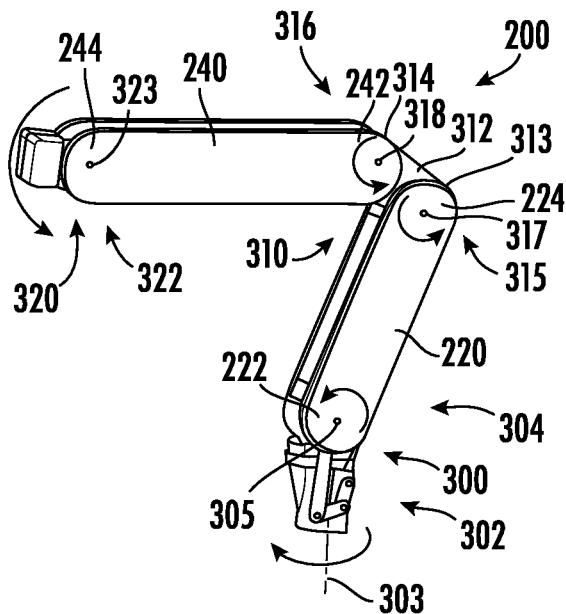
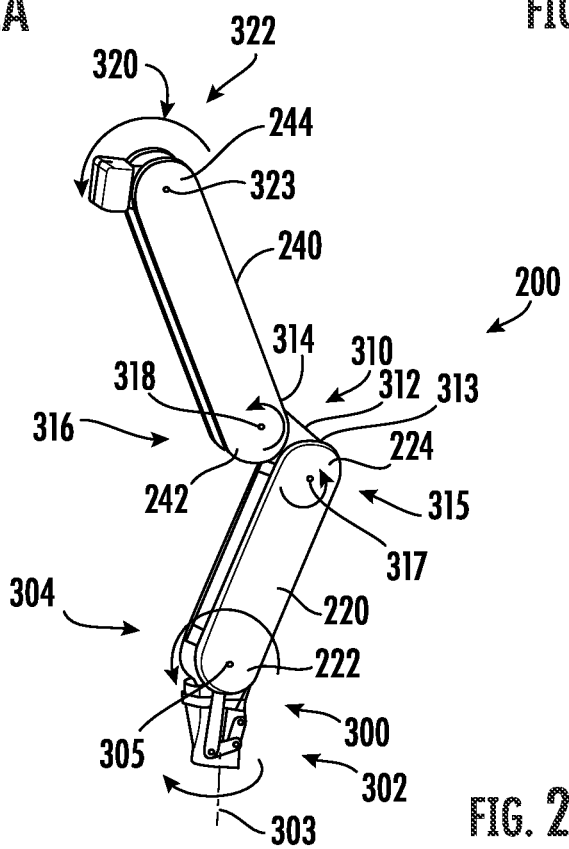
FIG. 2A
FIG. 2B
FIG. 2C

MINI C-ARM WITH INCREASED RANGE OF MOTION

This application is a United States National Phase filing of International Application No. PCT/US2019/053144, titled "Mini C-arm with Increased Range of Motion", filed Sep. 26, 2019, which is a non-provisional of, and claims the benefit of the filing date of, U.S. provisional patent application No. 62/738,149, filed Sep. 28, 2018, titled "Mini C-arm with Increased Range of Motion", the entirety of both applications are incorporated by reference herein.

FIELD OF THE DISCLOSURE

The present invention generally relates to imaging systems, and, more particularly, to a mobile imaging system such as, for example, a mini C-arm having increased range of motion.

BACKGROUND OF THE DISCLOSURE

Mobile imaging systems or mini C-arms as they are generally referred to provide non-invasive means for imaging a patient's bone and/or tissue. A conventional imaging system or mini C-arm includes a mobile base, an arm assembly, and a C-arm assembly including an X-ray source and a detector. The range of motion of the C-arm assembly, as provided by, for example, the arm assembly, controls the operator's ability to position the C-arm assembly relative to the patient. Limitations in the ability to position the C-arm assembly can inhibit the operator's ability to image the patient in certain positions. Accordingly, it is desirable to have a C-arm with an increased range of motion. It is with respect to these and other considerations that the present improvements may be useful.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is an imaging apparatus or system providing an increased range of motion. The imaging apparatus including a C-arm assembly including an X-ray source and a detector, a movable base, and an arm assembly coupling the C-arm assembly and the movable base, wherein the arm assembly is coupled to the movable base via a first joint assembly that enables the arm assembly to move relative to the moveable base about first and second axes of rotations. In one embodiment, the first axis of rotation is orthogonal to the second axis of rotation. In one embodiment, the first axis of rotation is a vertical axis of rotation so that the arm assembly can rotate or pivot relative to the movable base and the second axis of rotation is a horizontal axis of rotation so that the arm assembly can rotate or pivot relative to the movable base.

In another embodiment, a mobile imaging apparatus or system is also disclosed. The mobile imaging apparatus including a C-arm assembly including an X-ray source and a detector, a movable base including a platform, and an arm assembly for coupling the C-arm assembly and the movable base, wherein the arm assembly is coupled to the movable base via a first joint assembly that enables the arm assembly to move relative to the moveable base about a first vertical axis of rotation and a second horizontal axis of rotation, the second horizontal axis of rotation being located at a vertically fixed position so that the second horizontal axis of rotation is positioned at a fixed height from a top surface of the platform.

In one embodiment, the first joint assembly includes first and second pivot joints so that the arm assembly can rotate relative to the base about a vertical axis of rotation passing through the first pivot joint and a horizontal axis of rotation passing through the second pivot joint.

In some embodiments, the arm assembly includes a first arm and a second arm, the first arm coupled to the second arm via a second joint assembly, the second joint assembly adapted and configured so that the second arm can pivot or rotate relative to the first arm. The second joint assembly may include a link arm including a first end and a second end, the first end of the link arm being coupled to a second end of the first arm via a third pivot joint so that the second arm can rotate or pivot relative to the first arm about a horizontal axis of rotation passing through the third pivot joint, the second end of the link arm being coupled to a first end of the second arm via a fourth pivot joint so that the second arm can rotate or pivot relative to the first arm about a horizontal axis of rotation passing through the fourth pivot joint.

In some embodiments, the arm assembly may be coupled to the C-arm assembly via a third joint assembly, the third joint assembly including fifth and sixth pivot joints so that the C-arm assembly can rotate or pivot about a horizontal axis of rotation passing through the fifth pivot joint and a vertical axis of rotation passing through the sixth pivot joint. In addition, the third joint assembly may include a seventh pivot joint so that the C-arm assembly can rotate or pivot about a horizontal axis passing through the seventh pivot joint.

In another embodiment, a mobile imaging apparatus or system is also disclosed. The mobile imaging apparatus including a C-arm assembly including an X-ray source and a detector, a movable base including a platform, and an arm assembly coupling the C-arm assembly and the movable base, the arm assembly including a first arm, a second arm, and a second joint assembly for coupling the first arm to the second arm, wherein the arm assembly is coupled to the movable base via a first joint assembly that enables the arm assembly to move relative to the moveable base about a first vertical axis of rotation and a second horizontal axis of rotation, the horizontal axis of rotation being located at a vertically fixed position so that the horizontal axis of rotation is positioned at a fixed height from a top surface of the platform.

BRIEF DESCRIPTION OF THE DRAWINGS

By way of example, a specific embodiment of the disclosed device will now be described, with reference to the accompanying drawings, in which:

FIGS. 2A-2E illustrate perspective views of an example embodiment of an arm assembly for use with the mobile imaging system or mini C-arm shown in FIG. 1; FIGS. 2A-2E illustrating first and second arms of the arm assembly located in various positions with respect to each other;

Figure 1:
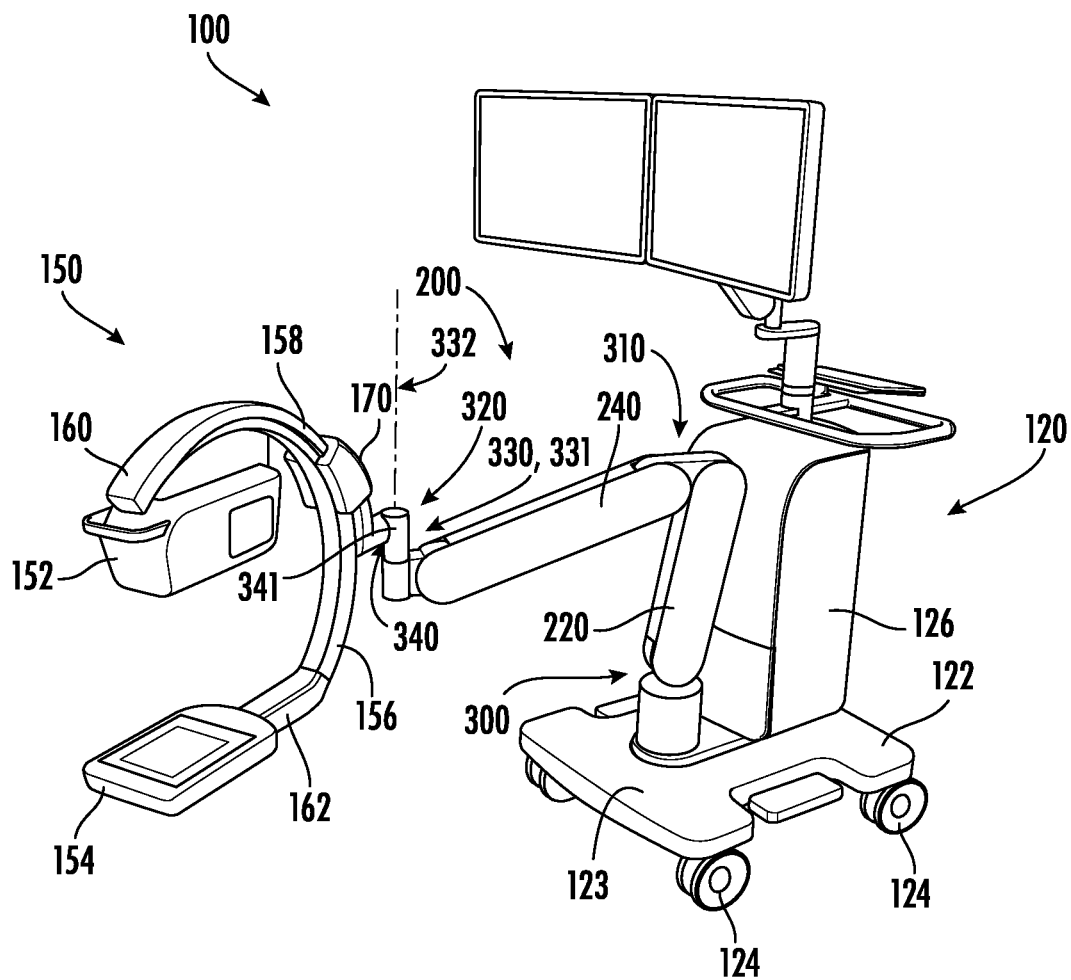
FIG. 1 is a perspective view of an example embodiment of a mobile imaging system or mini C-arm according to the present disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

DETAILED DESCRIPTION

Numerous embodiments of a mobile imaging system or mini C-arm (used interchangeably herein without the intent to limit) in accordance with the present disclosure will now be described more fully hereinafter with reference to the accompanying drawings, in which preferred embodiments of the present disclosure are presented. The mini C-arm of the present disclosure may, however, be embodied in many different forms and should not be construed as being limited to the embodiments set forth herein. Rather, these embodiments are provided so that this disclosure will convey certain example aspects of the mini C-arm to those skilled in the art. In the drawings, like numbers refer to like elements throughout unless otherwise noted.

Conventional mini C-arms suffer from limited range of motion. As a result, operators are generally limited in their ability to position the imaging components (e.g., X-ray source and detector). For example, conventional mini C-arms limit the operator's ability to position the X-ray source and detector close to the floor limiting the operator's ability to scan, for example, a standing knee, ankle or foot (e.g., limits the operator's ability to image a floor-standing weight-bearing knee or a lateral floor-standing ankle). In use, when imaging a patient's ankle, the injured patient may be required to stand on a step to accommodate the imaging components (e.g., X-ray source and detector). This requires the patient to stand, placing additional weight on the patient's injured, for example, foot, ankle, etc.

For example, one known mini C-arm includes a base or cabinet, an imaging assembly (e.g., an x-ray source and an x-ray sensor), and an arm assembly for connecting the imaging assembly to the cabinet. In use, the arm assembly is connected to the cabinet via a shoulder joint so that the arm assembly can vertically and rotationally move relative to the cabinet. That is, the shoulder joint includes a vertically extending rod coupled to the cabinet so that the arm assembly can be moved vertically along a length of the rod (and hence the cabinet) thus providing movement in a vertical direction along a longitudinal axis of the rod. One drawback of this prior art system is that by coupling the arm assembly to the cabinet along a slidably, vertical position, the operator's ability to position the imaging assembly close to the floor is limited.

In contrast, in accordance with one aspect of the present disclosure, the mini C-arm of the present disclosure is adapted and configured to provide an increased range of motion so that the imaging components (e.g., X-ray source and detector) can be positioned closer to the floor to eliminate, or at least minimize, the required height of the step. By providing an increased range of motion, in particular, an increased vertical range of motion, the operator is provided with increased versatility in positioning the imaging components relative to the patient. For example, in one embodiment, the mini C-arm allows the operator to position the imaging components anywhere along the length of the patient, for example, the imaging components can be positioned closer to the floor to image the patient's foot, ankle, knee, etc. while still enabling the imaging components to be positioned adjacent to the shoulder area. By providing an increased range of motion, the mini C-arm according to the present disclosure provides increased versatility.

In accordance with one aspect of the present disclosure, as will be described in greater detail below, the mini C-arm of the present disclosure includes a C-arm assembly including an X-ray source and a detector, a movable or mobile base or the like, and an arm assembly for coupling the C-arm assembly and the movable base. In some embodiments, the arm assembly is coupled to the movable base via a first joint assembly that enables the arm assembly to move relative to the moveable base about first and second axes of rotation. That is, the arm assembly is coupled to the base via a first joint assembly that includes first and second pivot joints that enables two degrees of motion—a first vertical pivoting or rotational movement and a second horizontal pivoting or rotational movement (pivot and rotate are used interchangeably herein without the intent to limit). As such, the first axis of rotation is a vertical axis of rotation passing through the first pivot joint so that the arm assembly can rotate or pivot relative to the movable base and the second axis of rotation is a horizontal axis of rotation passing through the second pivot joint so that the arm assembly can rotate or pivot relative to the movable base. By providing a first vertical rotational movement and a second horizontal rotational movement, the arm assembly is adapted and configured to provide an increased range of motion.

Additionally, the second pivot joint is coupled to the base at a vertically fixed position so that the horizontal axis of rotation passing through the second pivot joint is positioned at a fixed height or distance from the base, and hence a fixed height or distance from the floor. By incorporating a first joint assembly that includes a second pivot joint that enables the arm assembly to be coupled to the base via a horizontal axis of rotation that is located at a vertically fixed position, the mini C-arm provides the operator with increased range of motion and increased versatility in positioning the imaging components (e.g., X-ray source and detector) relative to a patient to provide a more convenient and accommodating system. In particular, the operator can position the imaging components closer to the floor to image the patient's foot, ankle, knee, etc. thereby eliminating, or at least minimizing, the height of the required step for imaging a patient's foot/ankle. By providing a mini C-arm with an increased range of motion, the operator may minimize the patient's risk of falling. Referring now to FIG. 1, an illustrative example embodiment of a mini C-arm 100 according to the present disclosure is shown. In use, the mini C-arm 100 is adapted and configured to provide an increased range of motion for positioning imaging components relative to a patient. As illustrated, the mini C-arm 100 includes a base 120, a C-arm assembly 150, and an arm assembly 200 for coupling the C-arm assembly 150 to the base 120.

Referring to FIG. 1, in one embodiment, the base 120 may include a platform 122 and a plurality of wheels 124 extending from a bottom surface of the platform 122 so that the base 120, and hence the mini C-arm 100, can be movably located by the operator as desired. In one example embodiment, the wheels 124 are selectably lockable by the user and are adapted and configured so that when in a locked state, the wheels 124 allow the operator to manipulate the arm assembly 200 without shifting the location or orientation of the base 120. The base 120 may also include a cabinet 126. In use, as will be appreciated by one of ordinary skill in the art, the cabinet 126 may be sized and configured for storing, for example, controls (not shown) for operating the mini C-arm 100, electrical components (not shown) needed for operation of the mini C-arm 100, counterweights (not shown) needed to balance extension of the C-arm assembly 150, a brake system, a cord wrap, etc. The cabinet 126 may also include, for example, a keyboard, one or more monitors, a printer, etc.

In use, the mini C-arm 100 of the present disclosure may be used with any suitable base 120 now known or hereafter developed. As such, details regarding construction, operation, etc. of the base 120 are omitted for sake of brevity of the present disclosure. In this regard, it should be understood that the present disclosure should not be limited to the details of the base 120 disclosed and illustrated herein unless specifically claimed and that any suitable base can be used in connection with the principles of the present disclosure. Referring to FIG. 1, and as previously mentioned, in one embodiment, the mini C-arm 100 also includes a C-arm assembly 150. The C-arm assembly 150 may be any suitable imaging system now known or hereafter developed. For example, as illustrated, the C-arm assembly 150 includes a source 152, a detector 154, and an intermediate body portion 156 for coupling to the source 152 and the detector 154. The source 152 and the detector 154 may be any suitable source and detector now known or hereafter developed. For example, the source 152 may be, for example, an X-ray source. The detector 154 may be, for example, a flat panel detector including, but not limited to, an amorphous silicon detector, an amorphous selenium detector, a plasma-based detector, etc. In use, the source 152 and detector 154 are adapted and configured to create an image of a patent's anatomy, such as for example a hand, a knee, an ankle, etc.

That is, as will be readily known by one of ordinary skill in the art, in use, the imaging components (e.g., X-ray source 152 and detector 154) receive photons, convert the photons/X-rays to a manipulable electrical signal that is transmitted to an image processing unit (not shown). The image processing unit may be any suitable hardware and/or software system, now known or hereafter developed to receive the electrical signal and to convert the electrical signal into an image. Next, the image may be displayed on a monitor or TV screen. The image can also be stored, printed, etc. The image may be a single image or a plurality of images.

Referring to the illustrated embodiment of FIG. 1, the intermediate body portion 156 of the C-arm assembly 150 may be configured to have a substantially "C" or "U" shape, although other shapes are envisioned. In the illustrated embodiment, the intermediate body portion 156 includes a body portion 158 and first and second end portions 160, 162 for coupling to the source and detector 152, 154, respectively. Additionally, the C-arm assembly 150 may include an orbital mount 170 for coupling to the arm assembly 200 as will be described in greater detail below. In use, the orbital mount 170 may be coupled to the body portion 158 of the intermediate body portion 156 so that the body portion 158, and hence the source and detector 152, 154, can rotate or orbit relative to the orbital mount 170 so that the operator is provided with increased versatility in positioning the imaging components relative to the patient. In use, the intermediate body portion 156 may be integrally formed. Alternatively, the arm 156 can be separately formed and coupled together.

In use, the mini C-arm 100 of the present disclosure may be used with any suitable C-arm assembly 150 now known or hereafter developed. As such, details regarding construction, operation, etc. of the C-arm assembly 150 including the source 152 and detector 154 are omitted for sake of brevity of the present disclosure. In this regard, it should be understood that the present disclosure should not be limited to the details of the C-arm assembly 150 disclosed and illustrated herein unless specifically claimed and that any suitable C-arm assembly can be used in connection with the principles of the present disclosure. Referring to FIG. 1, and as previously mentioned, in one embodiment, the mini C-arm 100 also includes an arm assembly 200 for coupling the C-arm assembly 150 to the base 120. In use, the arm assembly 200 is adapted and configured to provide an increased range of motion so that the C-arm assembly 150 can be positioned as needed by the operator. The positioning may be performed manually by the operator.

Referring to FIGS. 1 and 2A-2E, the illustrated example embodiment of the arm assembly 200 includes a first arm 220 and a second arm 240, although it is envisioned that the arm assembly 200 may include a greater number of arms such as, for example, three, four, etc. The first arm 220 and the second arm 240 are substantially linear. As will be described in greater detail below, the first arm 220 may be coupled to the base 120 via a first joint assembly 300, the first joint assembly 300 may include first and second pivot joints 302, 304 so that the first arm 220, and hence the arm assembly 200 and the C-arm assembly 150, can move relative to the base 120, and more specifically, so that the first arm 220 can rotate or pivot about a vertical axis of rotation 303 passing through the first pivot joint 302 and a horizontal axis of rotation 305 passing through the second pivot joint 304. Incorporating a vertical axis of rotation 303 that passes through the first pivot joint 302 enables the arm assembly 200 to pivot or rotate to either side of the base 120, thus enabling the patient to be positioned on either side of the base 120 without having to move the base 120 to reach the patient.

Figure 2D:
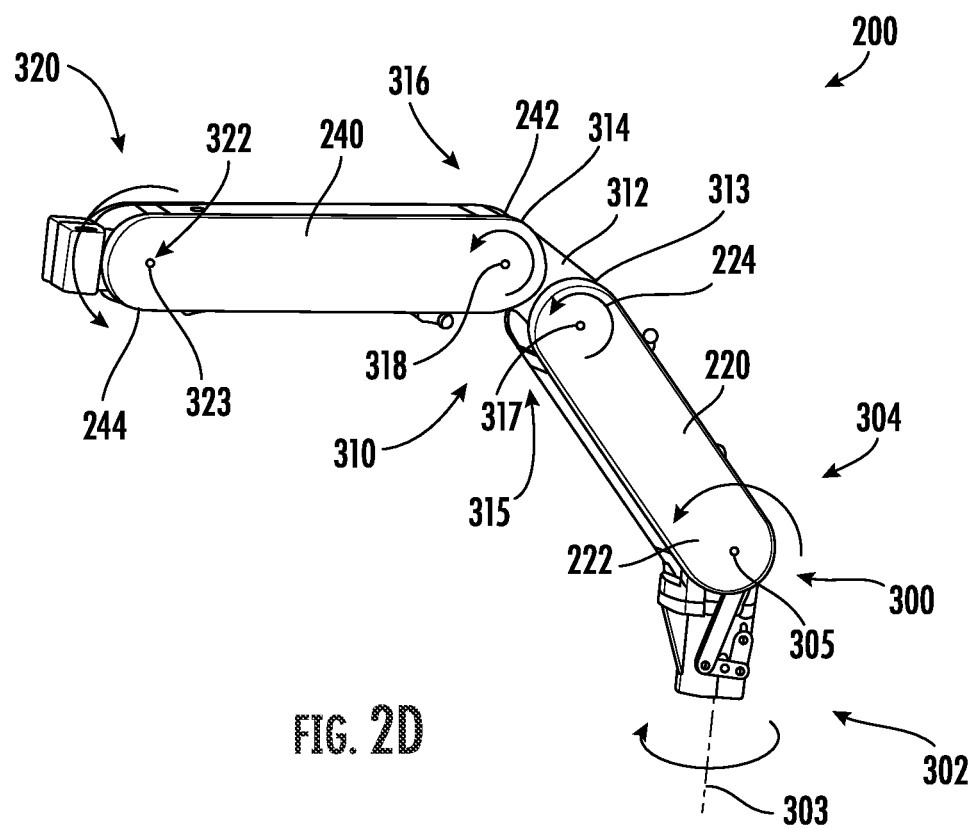
Figure 2E:
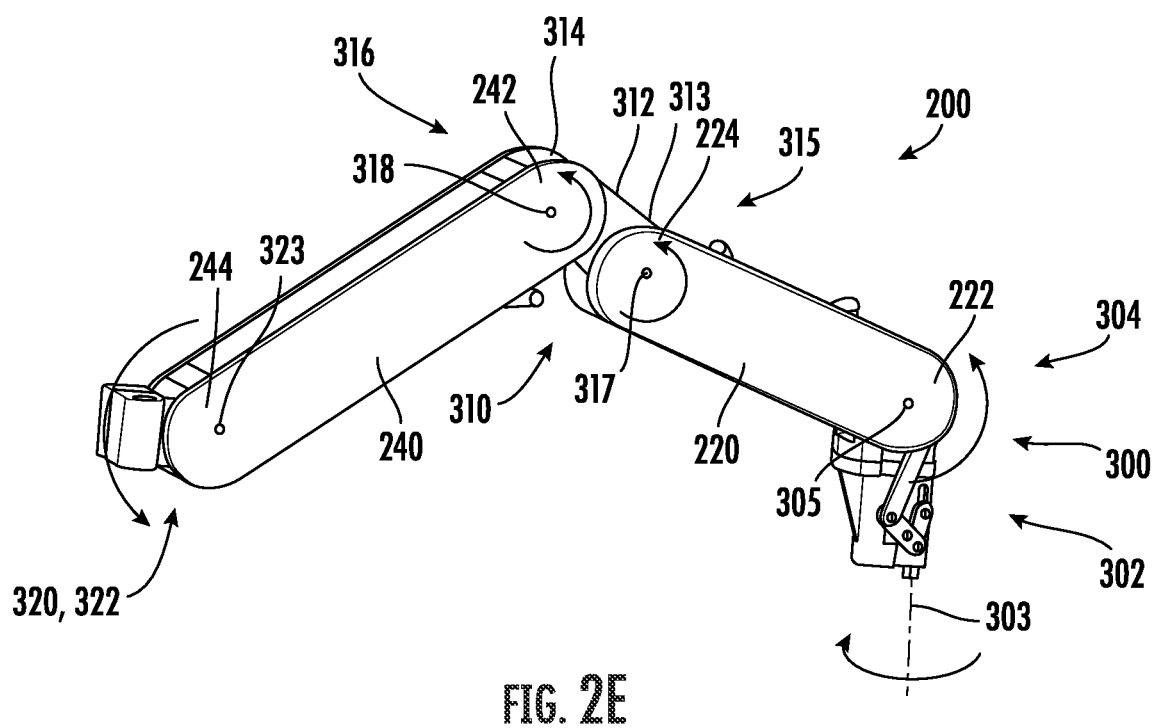

As best illustrated in FIGS. 2A-2E, the first and second arms 220, 240 are movably positionable relative to each other. As illustrated, first arm 220 may include a first end 222 and a second end 224. Similarly, the second arm 240 may include a first end 242 and a second end 244. The first and second arms 220, 240 may be coupled to each other by any mechanism now known or hereafter developed. As shown, the first end 242 of the second arm 240 is coupled to the second end 224 of the first arm 220. For example, as illustrated, the first and second arms 220, 240 may be coupled to each other via a second joint assembly 310. In use, the second joint assembly 310 may include a link arm 312. In use, the second end 224 of the first arm 220 may be coupled to a first end 313 of the link arm 312 via a third pivot joint 315 and the first end 242 of the second arm 240 may be coupled to the second end 314 of the link arm 310 via a fourth pivot joint 316, although, as previously mentioned, the first and second arms 220, 240 may be coupled by alternate mechanisms such as, for example, the first arm may be directly, pivotably coupled to the second arm (e.g., without the intervening link arm). In use, the third and fourth pivot joints 315, 316 enable the second arm 240 to move relative to the first arm 220, and more specifically, enable the second arm 240 to rotate or pivot about horizontal axes 317, 318 passing through the third and fourth pivot joints 315, 316, respectively. As such, axis 317 enables the link arm 312 and the second arm 240 coupled thereto to rotate or pivot relative to the first arm 220. Similarly, axis 318 enables the link arm 312 and the first arm 220 coupled thereto to rotate or pivot relative to the second arm 240. Incorporating a dual axes joint assembly provides the operator with increased versatility in positioning the imaging components (e.g., X-ray source and detector) relative to the patient. For example, the dual axes joint assembly allows for the first and second arms 220, 240 to be folded close together (e.g., as shown in FIG. 2A). This allows for the arm assembly 200 to be folded closer to the base 120 for imaging the patient's extremity closer to the base 120. Additionally, the second joint assembly 310 allows for positioning the imaging components closer to the floor for imaging a standing ankle or knee. In some embodiments, it is envisioned that the second joint assembly may also be adapted and configured to enable the first and second arms to rotate about a vertical axis of rotation passing through the second joint assembly.

Additionally, as illustrated, in one embodiment, the second end 244 of the second arm 240 may be coupled to the C-arm assembly 150 via a third joint assembly 320. For example, in one embodiment, the second end 244 of the second arm 240 may be pivotably coupled to the orbital mount 170 via a fifth pivot joint 322 so that the C-arm assembly 150 can pivot about a horizontal axis of rotation 323 passing through the fifth pivot joint 322. Additionally, as will be appreciated by one of ordinary skill in the art, the second end 244 of the second arm 240 may be coupled to the C-arm assembly 150 via an interconnecting articulating joint assembly 330 (FIG. 1). In use, the articulating joint assembly 330 includes a sixth pivot joint 331 adapted and configured to enable the C-arm assembly 150 to rotate about a vertical axis of rotation 332 passing through the sixth pivot joint 331 (FIG. 1). In this manner, by pivotably coupling the second end 244 of the second arm 240 to the articulating joint assembly 330, the C-arm assembly 150 is able to pivot or rotate about a horizontal axis of rotation 323 passing through the fifth pivot joint 322 and rotationally pivot or rotate about the vertical axis of rotation 332 passing through the sixth pivot joint 331 to provide the operator with increased versatility in positioning of the C-arm assembly 150 relative to the patient. Although it is envisioned that the arm assembly 200 may be coupled to the C-arm assembly 150 via any other mechanism including, for example, pivotally coupling the C-arm assembly 150 to the second end 244 of the second arm 240. Additionally, the third joint assembly 320 may also include a seventh pivot joint 340 (FIGS. 1 and 3) that enables the C-arm assembly 150 to rotate or pivot about a horizontal axis of rotation 341 that passes through the seventh pivot joint 340 to enable the C-arm assembly to rotate or pivot between upright and lateral positions (e.g., between vertical and lateral planes), as illustrated in positions A and B of FIG. 3 and position C of FIG. 3).

Referring to FIGS. 1, and 2A-2E, and as previously mentioned, in one embodiment, the arm assembly 200 is coupled to the base 120 via a first joint assembly 300. As will be described in greater detail, the first joint assembly 300 may be any mechanism configured to enable the arm assembly 200 to pivot or rotate relative to the base 120 about, inter alia, a horizontal axis of rotation. For example, as illustrated and as previously mentioned, the first joint assembly 300 may include first and second pivot joints 302, 304 so that the arm assembly 200, and hence the C-arm assembly 150, can move relative to the base 120. More specifically, in use, the first pivot joint 302 enables the arm assembly 200 to rotate or pivot about a vertical axis of rotation 303 passing through the first pivot joint 302 and to rotate or pivot about a horizontal axis of rotation 305 passing through the second pivot joint 304. In this manner, the arm assembly 200 may pivot or rotate relative to the base 120 about two axes of rotation, a vertical axis of rotation and a horizontal axis of rotation. In one embodiment, the two axes of rotation are orthogonal with respect to each other. By providing a first vertical rotational movement and a second horizontal rotational movement, the arm assembly 200 is adapted and configured to provide an increased range of motion. For example, rotation about the vertical axis 303 allows lateral or side-to-side range of motion of the C-arm, while rotation about the horizontal axis 305 contributes to motion in a vertical plane (e.g., simultaneously in-out and up-down relative to the base 120).

Figure 3:
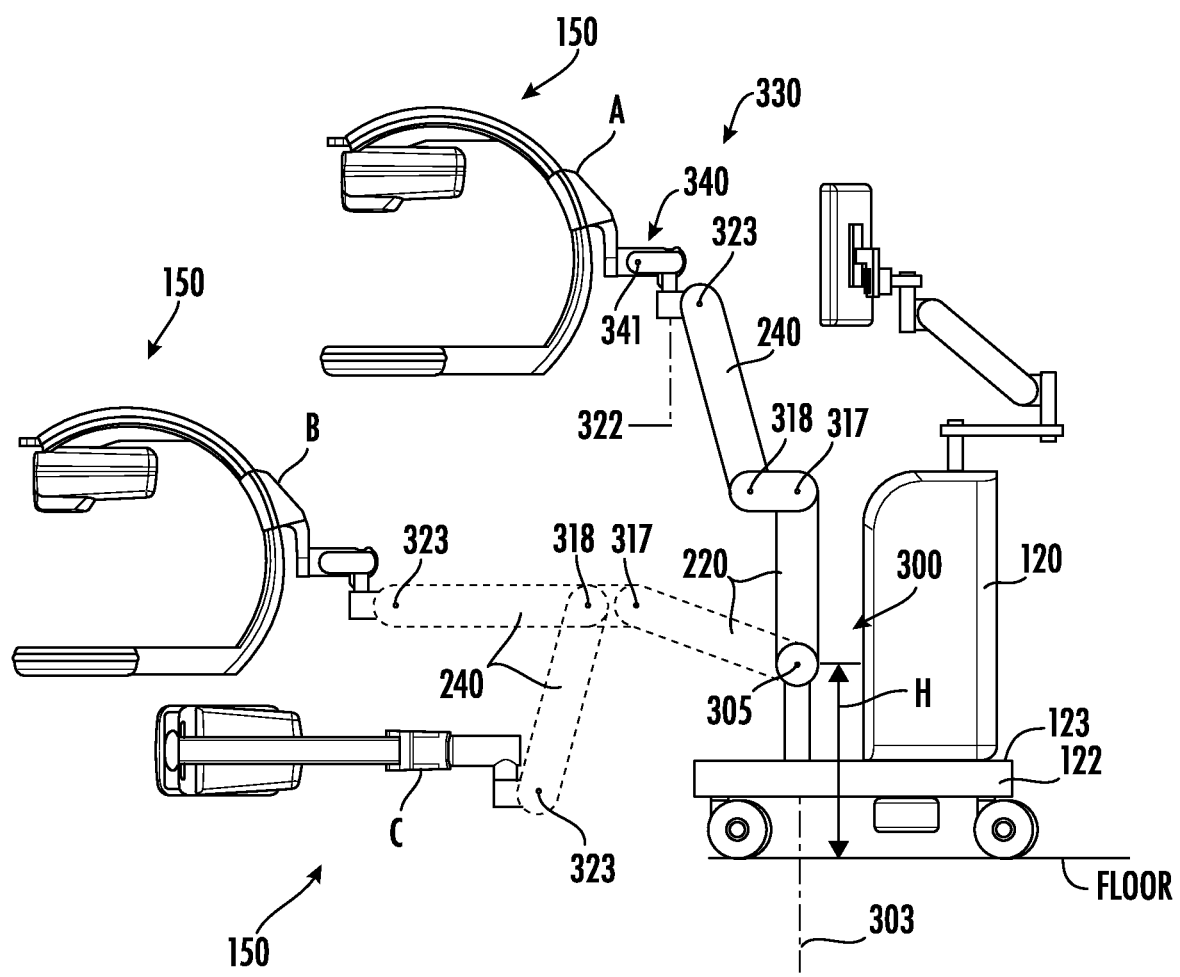
FIG. 3 is a side view of the mobile imaging system or mini C-arm shown in FIG. 1, the mobile imaging system or mini C-arm shown in a variety of different possible positions.

As such, in contrast with known mini C-arm assemblies that couple the arm assembly to the base via a vertically adjustable connection and thus limited in their ability to position the imaging components close to the floor, the arm assembly 200 of the present disclosure is coupled to the base 120 via a joint assembly such as, for example, the first joint assembly 300, that is positioned at a fixed height from a top surface 123 of the platform 122, and hence a fixed height H from the floor. As shown in FIG. 3, the C-arm assembly 150 is positioned in a variety of different possible positions. For example, as shown in the illustrated embodiment, the C-arm assembly 150 may be positioned to image a standing shoulder of a patient. In one example embodiment, the C-arm may be rotated to image the standing shoulder (e.g., C-arm may be rotated as schematically illustrated in position C). In one example embodiment, the C-arm may reach a vertical height, as measured from the floor to the center of rotation of the C-arm, of approximately 55 to 59 inches, with a preferred height of approximately 56.2 inches. In addition, and/or alternatively, in one example embodiment, referring to position B, the C-arm assembly 150 may be arranged and configured with a horizontal reach of approximately 55 to 62 inches, with a preferred horizontal reach of approximately 55 inches to image for example, a patient laying on an operating table or a hand or elbow positioned at the patient's position of those extremities and the C-arm assembly 150 is shown to reach the fixed height of 10½ inches from the floor in the position C to image a standing ankle of a patient. That is, in accordance with one of the principles of the present disclosure, the mini C-arm 100 includes an arm assembly 200 that is coupled to the base 120 via a rotatable or pivotable connection that is located at a vertically fixed position (e.g., while the first joint assembly 300 enables the arm assembly 200 to rotate about a horizontal axis of rotation 305 and a vertical axis of rotation 303, the position of the horizontal axis of rotation 305 is fixed relative to the base 120 (e.g., a fixed distance or height from the top surface 123 of the platform 122, and hence a fixed distance or height H from the floor)).

Figure 4:
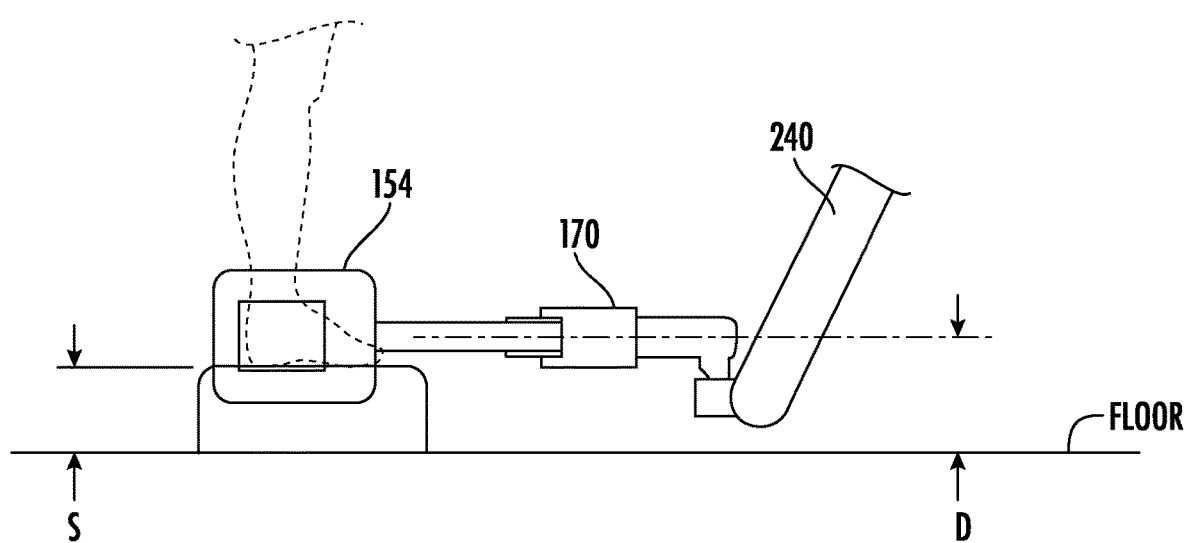
FIG. 4 is a partial, schematic side view of the mobile imaging system or mini C-arm shown in FIG. 1, the mobile imaging system or mini C-arm being positioned to image a patient's ankle.

By providing a fixed distance or height between the horizontal axis of rotation 305 of the first joint assembly 300 and the top surface 123 of the platform 122, and hence a fixed distance or height H from the floor, the arm assembly 200 provides an increased range of motion that is suited for positioning closer to the floor to image, for example, the patient's ankle. Referring to FIG. 4, it has been found that by providing a fixed distance or height (FIG. 3) between the horizontal axis of rotation 305 of the first joint assembly 300 and the top surface 123 of the platform 122, and hence a fixed distance or height H from the floor, the mini C-arm 100 is capable of positioning the center of the detector a distance D from the floor, which, in use, requires a step S for imaging a patient's ankle. In one embodiment, the minimum fixed distance or height H from the floor to the horizontal axis of rotation 305 may be approximately 15 inches. The maximum length of the first arm 220 may be approximately 17 inches while the maximum length of the second arm 240 may be approximately 21 inches. As a result, it has been found that the imaging components may be positioned at a distance D of approximately 10½ inches from the floor, requiring approximately a 6-inch step S for imaging a patient's ankle. In another embodiment, it has been found that the distance D may be approximately 4½ inches from the floor, requiring approximately a 2-inch step S for imaging a patient's ankle.

By providing an arm assembly 200 in accordance with the present disclosure, and specifically, by providing a fixed distance or height between the horizontal axis of rotation 305 of the first joint assembly 300 and the top surface 123 of the platform 122, and hence a fixed distance or height H from the floor, it has been found that the arm assembly 200 provides an increased range of motion that is suited for positioning closer to the floor to image, for example, the patient's ankle (position C in FIG. 3), while still enabling imaging of the patient's shoulder area (position A in FIG. 3).

Additionally, in some embodiments, to control movement of the arm assembly 200 and prevent the risk of tipping, especially as the arm assembly 200 is rotated laterally about the vertical axis of rotation 303, the mini C-arm 100 may include one or more stop mechanisms for controlling or limiting the movement of the arm assembly 200. That is, for example, in use, as the arm assembly 200 is fully extended, the size and weight of the base 120 can be configured to prevent the mini C-arm 100 from tipping forwards about the front wheels 124. For example, in one embodiment, the base 120 may be provided with counterweights to prevent forward tipping. However, due to limitations in size (e.g., ability to pass through a doorway), lateral or sideways rotation of the arm assembly 200 should be constrained to prevent sideways tipping of the mini C-arm 100. For example, fully extending the arm assembly 200 while placing the C-arm assembly 150 in a lateral or side position could cause the mini C-arm 100 to tip. To prevent or limit placement of the C-arm assembly 150, one or more stop mechanisms may be incorporated to limit the extension and/or lateral displacement of the arm assembly 200. The stop mechanisms may be any suitable mechanisms now known or hereafter developed and may be in the form of one or more mechanical stops. Alternatively, the stops may be in the form of software which limits the movement of the arm assembly 200. For example, if the arm assembly 200 is being positioned in such a manner to create a tipping hazard, the software may automatically raise the arm assembly 200 as the arm assembly 200 is being further extended. Similarly, mechanical stops may be incorporated which prevent the arm assembly 200 from being overly extended in such as a manner as to create a tipping hazard.

In one embodiment, the arm assembly 200 may include an anti-tipping mechanism adapted and configured to prevent tipping of the mini C-arm 100 by limiting the range of motion of the arm assembly 200, especially lateral or sideways rotation of the arm assembly 200 when the C-arm assembly 150 is outwardly extended beyond a predetermined position or angle.

Referring to FIGS. 5A-5D, the arm assembly 200 may include a linkage assembly 400. In use, the linkage assembly 400 is adapted and configured to convert angular rotation of the arm assembly 200 into vertical displacement or movement of a stop shaft 450 so that, for example, lateral or sideways rotation of the arm assembly 200, in combination with the arm assembly 200 being angularly rotated beyond the predetermined position or angle, is limited or constrained. That is, as will be described in greater detail, the stop shaft 450 is movably or slidably coupled relative to a base portion 155 of the arm assembly 200. In use, the stop shaft 450 is vertically displaceable relative to the base portion 155 so that when the stop shaft 450 descends below a bottom plane 460 of the base portion 155, lateral or sideways rotation of the arm assembly 200 about the vertical axis of rotation 303 is limited by a corresponding pocket (not shown) formed in the platform 122 of the base 120. In the illustrated example embodiment of FIGS. 5A-5D, the linkage assembly 400 includes a first bar or link (used interchangeably herein) 410 coupled to the stop shaft 450, a second bar 420 pivotably coupled to the first bar 410, and a third bar 430 pivotably coupled to the second bar 420 and the first arm 220 of the arm assembly 200. That is, in the illustrated example embodiment, the stop shaft 450 is slidably coupled to the base portion 155 of the arm assembly 200 and pivotably coupled to the first bar 410. The first bar 410 is pivotably coupled to the stop shaft 450 and the second bar 420. The second bar 420 is pivotably coupled to the first bar 410, the base portion 155, and the third bar 430. The third bar 430 is pivotably coupled to the second bar 420 and the first arm 220 of the arm assembly 200. In use, the platform 122 of the base 120 includes a pocket (not shown) for receiving the stop shaft 450 (e.g., end portion 452 (FIGS. 5C and 5D) of the stop shaft 450 that extends vertically beyond the bottom plane 460 of the base portion 155).

Figure 5A:
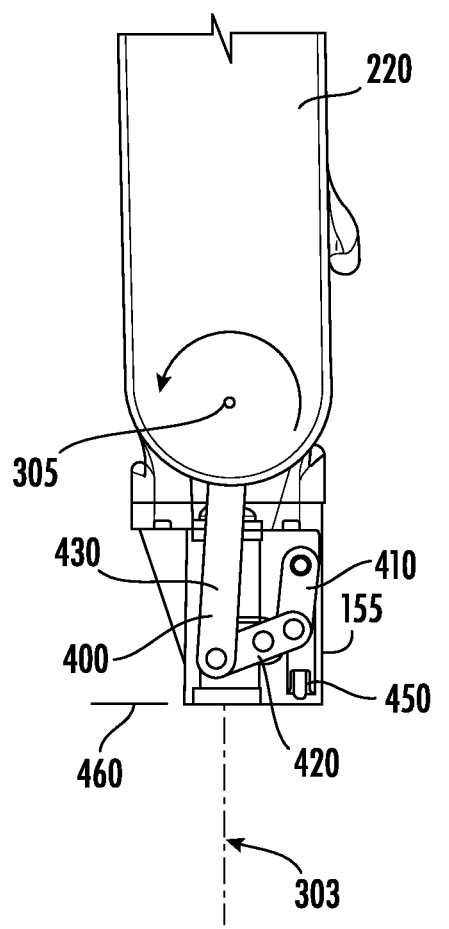
FIGS. 5A-5D illustrate side views of an example embodiment of an anti-tipping mechanism that may be used in connection with the mobile imaging system or mini C-arm shown in FIG. 1, FIGS. 5A-5D illustrating the anti-tipping mechanism in various positions.
Figure 5B:
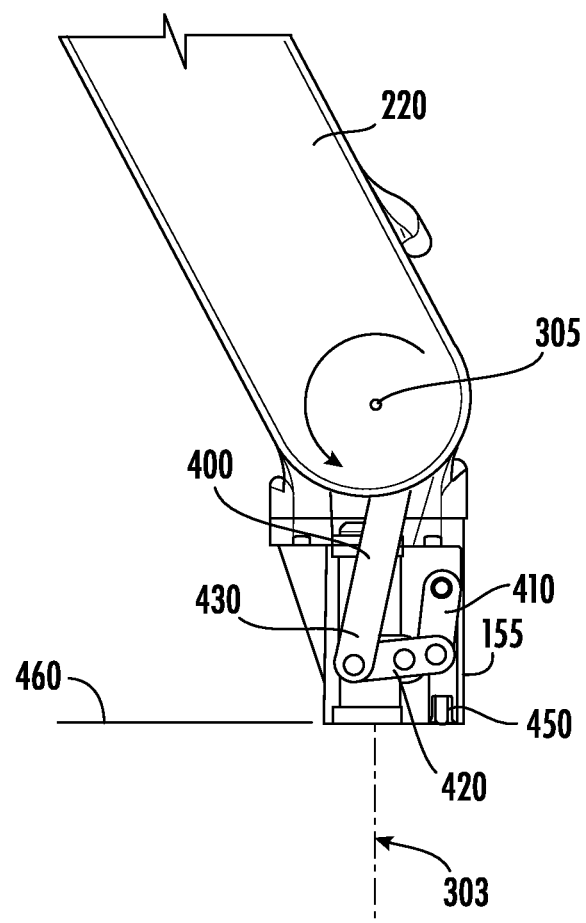
Figure 5C:
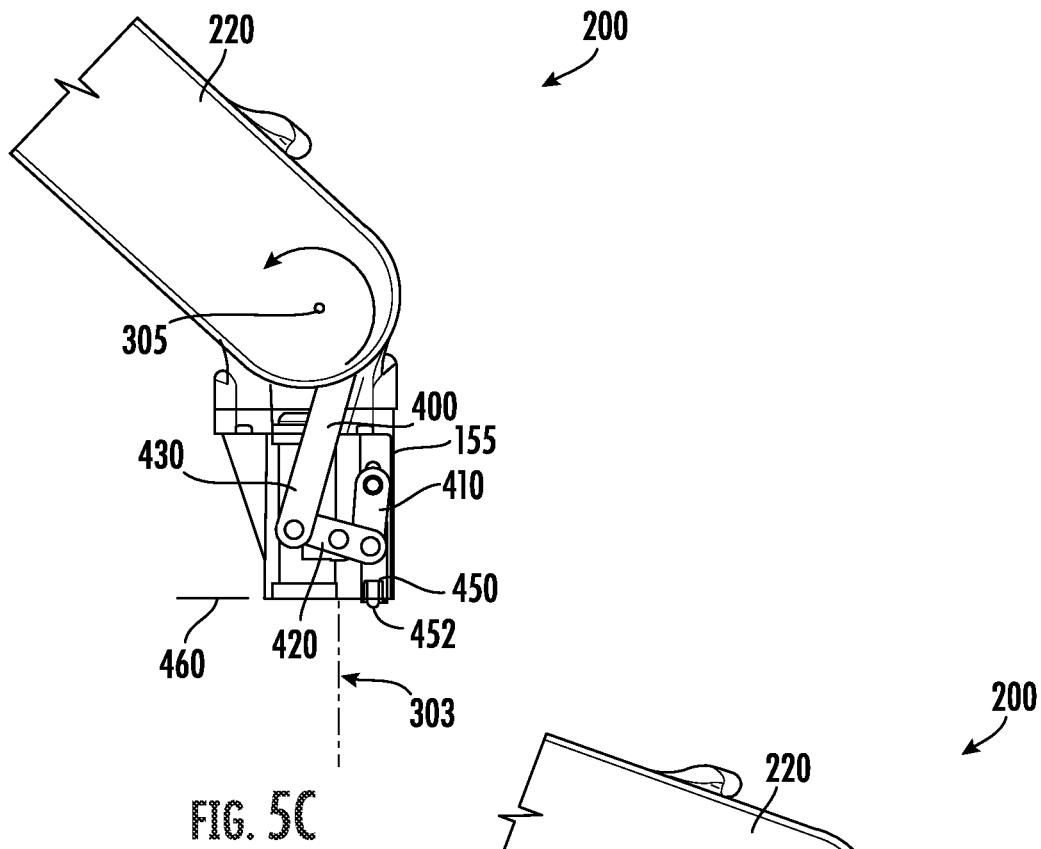
Figure 5D:
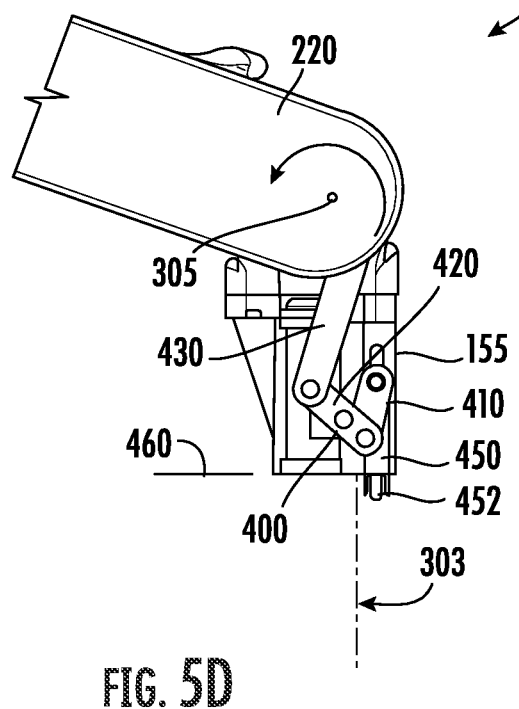

In use, angular rotation of the first arm 220 of the arm assembly 200 about the horizontal axis of rotation 305 causes the first bar 410 of the linkage mechanism 400 to move downwards relative to the base portion 155 as illustrated by comparing FIGS. 5A-5D. This in turn causes the stop shaft 450 to move vertical downwards relative to the base portion 155. As the first arm 220 of the arm assembly 200 is rotated beyond a predetermined angle, the stop shaft 450 moves vertical downwards until an end portion 452 passes below a bottom plane 460 of the base portion 155 (as illustrated in FIGS. 5C and 5D).

Referring to FIGS. 5A and 5B, with the first arm 220 of the arm assembly 200 being positioned within a predetermined angle of rotation about the horizontal axis of rotation 305, the end portion 452 of the stop shaft 450 is located within the base portion 155 (e.g., located above the bottom plane 460 of the base portion 155). As a result, movement of the arm assembly 200 is unrestricted as the stop shaft 450 does not contact the pocket formed in the platform 122 of the base 120. That is, with the angular rotation of the first arm 220 of the arm assembly 200, about the horizontal axis of rotation 305, being within a predetermined angle of rotation, lateral rotation of the arm assembly 200 about the vertical axis of rotation 303 is uninhibited.

However, referring to FIGS. 5C and 5D, as the first arm 220 of the arm assembly 200 is further rotated about the horizontal axis of rotation 305 so that the angular position of the first arm 220 begins to exceed the predetermined angle of rotation, the end portion 452 of the stop shaft 450 extends beyond the bottom plane 460 and extends into the pocket formed in the platform 122 of the base 120. In this position, lateral rotation of the arm assembly 200 about the vertical axis of rotation 303 causes the stop shaft 450 to contact the pocket and thus lateral or sideways movement of the arm assembly 200 is inhibited and/or prevented. In one example embodiment, with the first arm 220 of the arm assembly 200 positioned outside of the predetermined angle of rotation, lateral rotation of the arm assembly 200 about the vertical axis of rotation 303 causes the end portion 452 of the stop shaft 450 to contact the pocket formed in the platform 122 of the base 120 thus force the stop shaft 450 to move vertical upwards resulting in the first arm 220 move angularly back into acceptable position.

During use, if the first arm 220 of the arm assembly 200 is moved angularly upwards so that the predetermined angle is no longer exceeded, the stop shaft 450 moves above the bottom plane 460 of the base portion 155 so that lateral or sideways rotation is no longer inhibited. However, with the arm assembly 200 rotated in the lateral position, if the first arm 220 of the arm assembly 200 is then rotated outwards about the horizontal axis of rotation 305, the stop shaft 450 will encounter a region of the platform 122 outside of the pocket, thus restricting or limiting angular rotation (e.g., lowering) of the first arm 220 beyond the bottom plane 460 thereby preventing full extension of the arm assembly 200. In this manner, the linkage assembly 400 and the pocket formed in the platform 122 of the base 120 are arranged and configured to selectively allow and prevent the stop shaft 450 from moving (e.g., extending vertically downwards beyond the bottom plane 460 of the base portion 155) depending on the location of the arm assembly 200. That is, the linkage assembly 400 and the pocket are arranged and configured to enable the stop shaft 450 to extend vertical downwards into the pocket when the arm assembly 200 is positioned within an acceptable range of motion. However, if the arm assembly 200 is being positioned such that extension of the arm assembly 200 is beyond an acceptable range, the linkage assembly 400 and the pocket are arranged and configured to prevent the stop shaft 450 from moving vertical downwards into the pocket and thus prevent the first arm 220 from pivoting beyond an acceptable angle. For example, in one illustrated embodiment, the pocket may be in the form of an opening having an arc shaped centered on the vertical axis of rotation 303 so that when the stop shaft 450 hits either end of the arc the base portion 155 and hence the arm assembly 200 are prevented from rotating any further.

As will be appreciated by one of ordinary skill in the art, the predetermined angle of rotation and the acceptable range of motion will vary depending on other characteristics of the mini C-arm 100. For example, the predetermined angle of rotation and the acceptable range of motion will be dependent on, inter alia, size and weight of the first and second arms 220, 240, the base 120, etc.

In accordance with another aspect of the present disclosure, the arm assembly 200 may include a self-balancing mechanism so that once the C-arm assembly 150 is positioned and orientated in its desired location, the first and second arms 220, 240 of the arm assembly 200 remain in their respective position without the need for a brake mechanism. That is, it is known for mini C-arms to incorporate a brake mechanism to hold or maintain the position of the arms. This is primarily due to the fact that in current mini C-arms, the force of gravity is not balanced with the spring force of the arm assembly as the arms are moved throughout their entire range of motion. Thus, a brake mechanism is provided to secure or lock the position of the arms.

Figure 6:
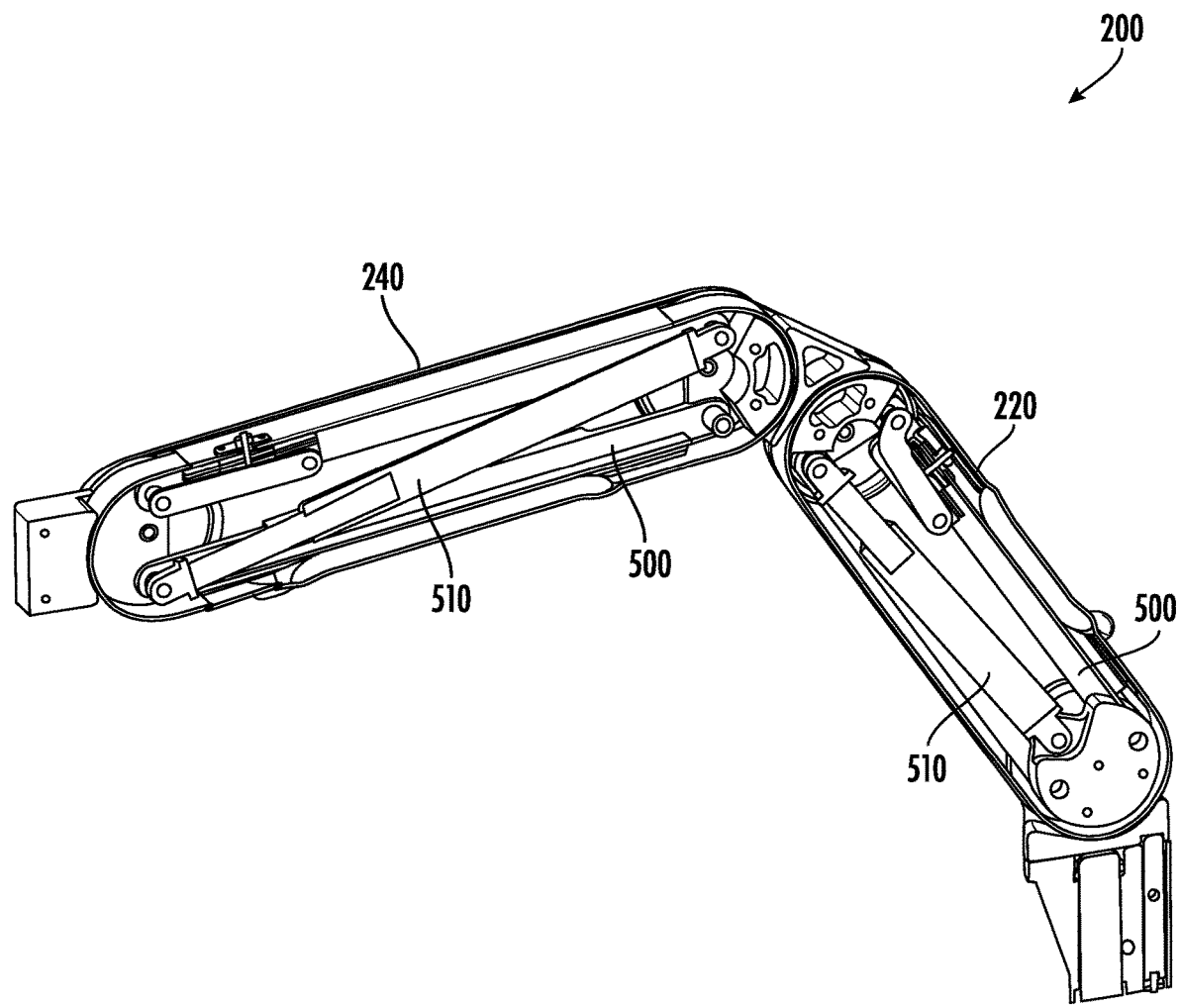
FIG. 6 illustrates a cross-section view of an example embodiment of a self-balancing mechanism that may be used in connection with the mobile imaging system or mini C-arm shown in FIG. 1.

Referring to FIG. 6, in one embodiment, the arm assembly 200 is adapted and configured to support and maintain the position and orientation of the C-arm assembly 150 without a brake assembly. That is, the arm assembly 200 is adapted and configured to maintain the position and orientation of the C-arm assembly 150 by balancing the spring forces within the arm assembly 200 against the force of gravity throughout the entire range of motion of the arm assembly 200. As illustrated, the first and second arms 220, 240 each include a four-bar mechanism 500 and an extension spring 510 to maintain the orientation and position of the C-arm assembly 150. Incorporation of a four-bar mechanism 500 into the first and second arms 220, 240 enables the orientation of the C-arm assembly 150 to be maintained as the arm assembly 200 moves throughout its range of motion. This is primarily due to the equal length sides of the four-bar mechanism 500. However, to ensure that the position of the C-arm assembly 150 is also maintained, an extension spring 510 is needed to balance against the forces of gravity. To this end, the first and second arms 220, 240 each include an extension spring 510.

As illustrated, the second arm 240 may include an extension spring 510 mounted across the diagonals of the four-bar mechanism 500. By correctly balancing the initial force and spring rate of the extension spring 510 to substantially match the force of gravity on the C-arm assembly 150, the arm assembly 200 can be made to maintain its position without the need to incorporate a brake assembly. It should be noted that variations in parts such as, for example, the weight of the C-arm assembly 150, the strength and stiffness of the spring 510, etc. means that the forces won't exactly match, however any variations would be small and can be masked by frictional forces in the arm assembly 200. As illustrated, the spring 510 positioned in the first arm 220 is offset from diagonal to accommodate the vertical axis of rotation.

While the present disclosure makes reference to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

What is claimed is:

1. An imaging apparatus comprising:
   a C-arm assembly including an X-ray source and a detector;
   a movable base; and
   an arm assembly coupling the C-arm assembly and the movable base, the arm assembly including a first arm and a second arm, the first arm disposed between the movable base and the second arm and the second arm is disposed between the first arm and the C-arm assembly;
   wherein the arm assembly is coupled to the movable base via a first joint assembly that enables the arm assembly to pivot relative to the movable base about first and second axes of rotations; and
   wherein the first arm is pivotably coupled to the second arm via a dual axis joint assembly, the dual axes joint assembly including a link arm pivotably coupled between the first arm and the second arm such that axes of the dual axes joint assembly are parallel.

2. The imaging apparatus of claim 1, wherein the first axis of rotation is orthogonal to the second axis of rotation.

3. The imaging apparatus of claim 1, wherein the first joint assembly includes first and second pivot joints so that the first axis of rotation is a vertical axis of rotation passing through the first pivot joint so that the arm assembly can rotate relative to the movable base and the second axis of rotation is a horizontal axis of rotation passing through the second pivot joint so that the arm assembly can pivot relative to the movable base.

4. The imaging apparatus of claim 1, wherein the axes of the dual axes joint assembly are horizontal axes.

5. The imaging apparatus of claim 1, wherein the second arm is coupled to the C-arm assembly via a third joint assembly.

6. The imaging apparatus of claim 5, wherein the third joint assembly is adapted and configured so that the C-arm assembly can pivot relative to the second arm.

7. The imaging apparatus of claim 6, wherein the third joint assembly includes at least one pivot joint.

8. A mobile imaging system comprising:
   a C-arm assembly including an X-ray source and a detector;
   a movable base including a platform; and
   an arm assembly for coupling the C-arm assembly and the movable base;
   wherein the arm assembly is coupled to the movable base via a first joint assembly that enables the arm assembly to move relative to the movable base about a first vertical axis of rotation and a second horizontal axis of rotation, the second horizontal axis of rotation being located at a vertically fixed position so that the second horizontal axis of rotation is positioned at a fixed height from a top surface of the platform;
   wherein the arm assembly includes a first arm and a second arm, the first arm coupled to the second arm via a second joint assembly; and
   wherein the second joint assembly includes a link arm including a first end and a second end, the first end of the link arm being coupled to a second end of the first arm via a third pivot joint so that the second arm can rotate relative to the first arm about a third horizontal axis of rotation passing through the third pivot joint, the second end of the link arm being coupled to a first end of the second arm via a fourth pivot joint so that the second arm can rotate relative to the first arm about a fourth horizontal axis of rotation passing through the fourth pivot joint, the third horizontal axis of rotation parallel to the fourth horizontal axis of rotation.

9. The mobile imaging system of claim 8, wherein the first joint assembly includes first and second pivot joints so that the arm assembly can rotate relative to the movable base, the first pivot joint including the first vertical axis of rotation, the second pivot joint including the second horizontal axis of rotation.

10. The mobile imaging system of claim 8, wherein a second end of the second arm is coupled to the C-arm assembly via a third joint assembly, the third joint assembly including a fifth pivot joint so that the C-arm assembly can rotate about a horizontal axis of rotation passing through the fifth pivot joint.

11. An imaging apparatus comprising:
    a C-arm assembly including an X-ray source and a detector;
    a movable base including a platform; and
    an arm assembly coupling the C-arm assembly and the movable base, the arm assembly including a first arm, a second arm, and a second joint assembly for coupling the first arm to the second arm;
    wherein the arm assembly is coupled to the movable base via a first joint assembly that enables the arm assembly to move relative to the movable base about a first horizontal axis of rotation and a second vertical axis of rotation, the first horizontal axis of rotation being located at a vertically fixed position so that the first horizontal axis of rotation is positioned at a fixed height from a top surface of the platform; and
    wherein the second joint assembly includes a link arm including a first end and a second end, the first end of the link arm being coupled to a second end of the first arm so that the second arm can rotate relative to the first arm about a second horizontal axis of rotation, the second end of the link arm being coupled to a first end of the second arm so that the second arm can rotate relative to the first arm about a third horizontal axis of rotation, the second horizontal axis of rotation parallel to the third horizontal axis of rotation.

12. The imaging apparatus of claim 11, wherein the second joint assembly is adapted and configured so that the second arm can pivot relative to the first arm.

13. The imaging apparatus of claim 11, wherein the second arm is coupled to the C-arm assembly via a third joint assembly adapted and configured so that the C-arm assembly can pivot relative to the second arm.

* * * * *